US006995147B2

(12) United States Patent
Escher et al.

(10) Patent No.: US 6,995,147 B2
(45) Date of Patent: Feb. 7, 2006

(54) METHOD OF DELAYING THE ONSET OF DIABETES

(75) Inventors: Alan P. Escher, Redlands, CA (US); Jingxue Liu, Concord, CA (US)

(73) Assignee: Loma Linda University, Loma Linda, CA (US)

( * ) Notice: Subject to any disclaimer, the term of this patent is extended or adjusted under 35 U.S.C. 154(b) by 143 days.

(21) Appl. No.: 10/257,221

(22) PCT Filed: Apr. 17, 2001

(86) PCT No.: PCT/US01/12392

§ 371 (c)(1),
(2), (4) Date: Oct. 7, 2002

(87) PCT Pub. No.: WO01/78771

PCT Pub. Date: Oct. 25, 2001

(65) Prior Publication Data

US 2005/0187173 A1      Aug. 25, 2005

Related U.S. Application Data

(60) Provisional application No. 60/198,137, filed on Apr. 17, 2000.

(51) Int. Cl.
*A01N 43/04*   (2006.01)
*A01N 63/00*   (2006.01)
*A01K 31/70*   (2006.01)
*A01K 65/00*   (2006.01)
*C07H 21/02*   (2006.01)

(52) U.S. Cl. .................. 514/44; 536/23.1; 536/23.4; 536/23.5; 424/93.1

(58) Field of Classification Search .............. 536/23.1, 536/23.4, 23.5, 24.1; 514/44; 424/93.1; 435/320.1
See application file for complete search history.

(56) References Cited

U.S. PATENT DOCUMENTS 6,001,360 A    12/1999   Atkinson et al. ........ 424/185.1
6,022,697 A    2/2000    Kaufman et al. .......... 435/7.24

FOREIGN PATENT DOCUMENTS

EP       0 519 469 A1    12/1992
WO       WO 92/15673 A    9/1992

OTHER PUBLICATIONS

Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Bowman, et al. (1994) Immunology Today, 15(3): 115-20.*
Filippova, et al. (2001) DNA Cell. Biol., 20(3):175-81.*
Winer, et al. (2002) J. Immunol., 168: 475-82.*
Cao, et al. (2004) J. Clin. Endocrinol. Metabol., 89(2): 898-903.*
Geng et al., "Widespread Expression of an Autoantigen-GAD65 Transgene Does Not Tolerize Non-Obese Diabetic Mice and Can Exacerbate Disease," Pro. Natl. Acad. Sci., USA, Aug. 1998, vol. 95, pp. 10055-10060.
Liu et al. "Intramuscular Injection of Plasmid DNA Encoding Intracellular or Secreted Glutamic Acid Decarboxylase Causes Decreased Insulitis in the Non-Obese Diabetic Mouse," Gene Ther. Mol. Biol., vol. 3, pp. 197-206, Aug. 1999.
Quintana et al., "Vaccination with Empty Plasmid DNA or CpG Oligonucleotide Inhibits Diabetes in Nonobese Diabetic Mice: Modulation of Spontaneous 60-kDA Heat Shock Protein Autommunity," J. Immunol., 2000, 165:6148-6155.
Sai et al., "Immunization of Non-Obese Diabetic (NOD) Mice with Glutamic Acid Decarboxylase-Derived Peptide 524-543 Reduces Cylophosphamide-Accelarated Diabetes," Clin. Exp. Immunol., Aug. 1996, vol. 105, No. 2, pp. 330-337.
Tisch et al., "Administering Glutamic Acid Decarboxylase to NOD Mice Prevents Diabetes," J. Autoimmun., 1994, vol. 7, pp. 845-850.
Tisch et al., "Antigen-Specific Mediated Suppression of β Cell Autoimmunity by Plasmid DNA Vaccination," J. Immunol., 2001, 166:2122-2132.
Weist-Ladenburger et al., "DNA Vaccination with Glutamic Acid Decarboxylase (GAD) Generates a Strong Humoral Immunuel Response in BALB/c, C57Bl/67, and Diabetes-Prone Mice, " Homr. Metab. Res. 1998, vol. 30, pp. 605-609.
Filippova et al., "Effects of plasmid DNA injection on cyclophosphamide-accelerated diabetes in NOD mice." DNA and Cell Biology, vol. 20, No. 3, 2001, pp. 175-181.
Roll U. et al., "DNA vaccination with plasmids containing GAD65 and/or interleukin-4 cDNA: No effect on the incidence of diabetes in NOD mice," Diabetologia, vol. 41, No. Suppl. 1, Aug. 1998, p. A87
Lorenz et al., "Isolation and Expression of a cDNA Encodig Renilla Reniformis Luciferase," Proceedings of the National Academy of Sciences of USA, National Academy of Science, Washington, US, vol. 88, May 1991, pp. 4438-4442.

* cited by examiner

*Primary Examiner*—Dave Trong Nguyen
*Assistant Examiner*—Robert M Kelley
(74) *Attorney, Agent, or Firm*—David A. Farah; Sheldon & Mak PC

(57) ABSTRACT

A method for preventing, delaying the onset of or treating diabetes in a patient comprising selecting a patient who is susceptible to developing diabetes, who is developing diabetes or who is diabetic and administering to the patient one or more than one dose of a pharmaceutical agent comprising a polynucleotide encoding a secreted exogenous protein, such as a secreted luciferase or a secreted form of human glutamic acid decarboxylase.

3 Claims, 1 Drawing Sheet

METHOD OF DELAYING THE ONSET OF DIABETES

CROSS-REFERENCE TO RELATED APPLICATIONS

Figure 1:
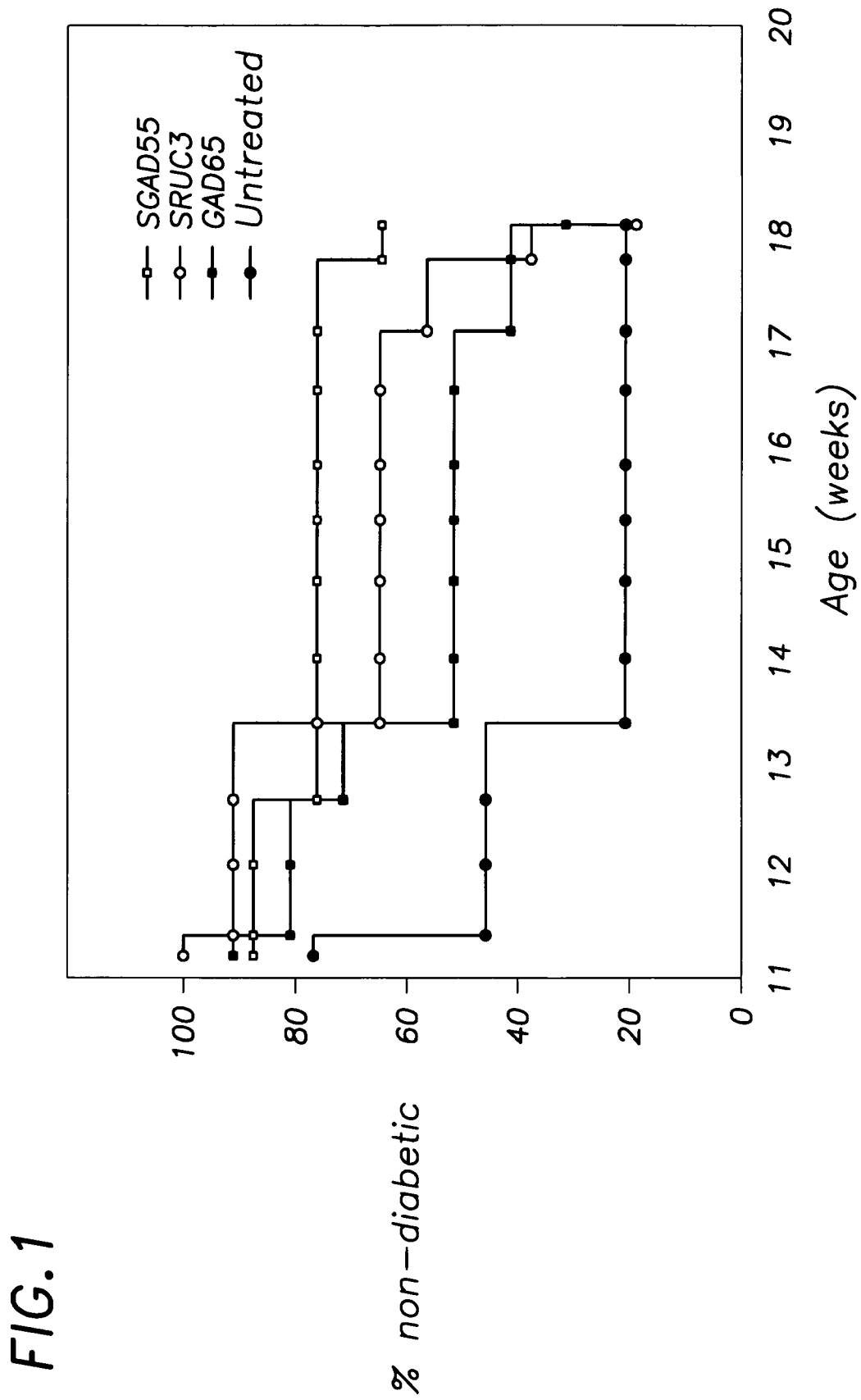

The present application takes priority from U.S. patent application 60/198,137, titled "Method for Preventing Diabetes," filed Apr. 17, 2000, the contents of which are incorporated herein by reference in their entirety.

STATEMENT REGARDING FEDERALLY SPONSORED RESEARCH OR DEVELOPMENT

This invention was made with United States Government support under Cooperative Agreement Number DAMD17-97-2-7016 with the National Medical Technology Testbed, Inc., United States Department of the Army. The United States Government has certain rights in this invention.

BACKGROUND

Diabetes is a major cause of morbidity and mortality in the United States and throughout the world. Diabetes is a metabolic disease characterized by the inability to metabolize glucose and generally divided into two types. Of the two types, type 1 diabetes usually results from autoimmune destruction of beta cells in the pancreas during adolescence which leads to insufficient insulin production.

Research into the causes and treatments for type 1 diabetes frequently involve the use of nonhuman animals. The non-obese diabetic (NOD) mouse is one animal model system generally accepted for studying type 1 diabetes as NOD mice develop a form of diabetes that parallels type 1 diabetes in humans, including sharing common susceptibility factors such as major histocompatibility complex molecules. Studies of NOD mice and humans have indicated that two proteins synthesized by pancreatic beta cells play determining roles as autoantigens responsible for the onset of diabetes. The two proteins are the hormone insulin, a secreted protein, and the enzyme glutamic acid decarboxylase (GAD), an intracellular protein found as either soluble GAD67, or membrane-bound GAD65 in beta cells. The importance of these two autoantigens for diabetes onset in NOD mice is indicated by the finding that most pathogenic CD8+ T cells recognize a single insulin epitope, and that mice with beta cell-specific reduced expression of gad65/67 genes do not develop diabetes. In humans, the presence of anti-insulin and anti-GAD autoantibodies has been used to predict the onset of diabetes. There remains, however, a need for a method of preventing diabetes in humans.

SUMMARY

According to the present invention, there is provided a method for preventing, delaying the onset of or treating diabetes in a patient. The method comprises, first, selecting a patient who is susceptible to developing diabetes, who is developing diabetes or who is diabetic. Next, the patient is administered one or more than one dose of a pharmaceutical agent comprising a polynucleotide encoding a secreted exogenous protein.

In a preferred embodiment, selecting the patient comprises identifying in the patient the presence of anti-insulin or anti-GAD autoantibodies, or identifying in the patient the presence of increasing hyperglycemia, or identifying in the patient the presence of glycosuria, or identifying in the patient the presence of a genetic predisposition to diabetes. In a particularly preferred embodiment, the one or more than one dose is a plurality of doses. In another particularly preferred embodiment, administering to the patient one or more than one dose comprises injecting the patient intramuscularly with the one or more than one dose. In another preferred embodiment, the method comprises, after administering, monitoring the patient for the development diabetes.

In a particularly preferred embodiment, the exogenous protein is a secreted *Renilla* luciferase comprising a sequence according to SEQ ID NO:1 or according to SEQ ID NO:3.

FIGURES

These and other features, aspects and advantages of the present invention will become better understood with regard to the following description, appended claims, and the accompanying figure where:

FIG. 1 is graph showing the percent on non-diabetic, cyclophosphamide treated NOD mice given versus time where the NOD mice were injected with plasmid DNA encoding full-length human GAD65 (filled boxes); SGAD55, a secreted form of human GAD65 (open boxes); SRUC3, a secreted form of the *Renilla reniformis* luciferase (open circles); or no injections of plasmid DNA (filled circles).

DESCRIPTION

According to one embodiment of the present invention, there is provided a method for delaying the onset of type 1 diabetes or preventing type 1 diabetes in a human or animal. The method comprises selecting a patient who is susceptible to developing diabetes or who is developing diabetes and administering to the patient one or more than one dose of a pharmaceutical agent. The pharmaceutical agent can comprise a polynucleotide encoding a secreted *Renilla* luciferase or can comprise, a polynucleotide encoding a secreted form of glutamic acid decarboxylase.

The present invention resulted from an investigation of cyclophosphamide-accelerated diabetes in non-obese diabetic (NOD) mice that were administered plasmid DNA encoding either intracellular human GAD, a secreted form of human GAD or a secreted form of *Renilla reniformis* luciferase. In summary, four-week old animals were injected with plasmid DNA encoding either intracellular human GAD, a secreted form of human GAD or a secreted form of *Renilla reniformis* luciferase. Animals injected with plasmid DNA encoding secreted GAD demonstrated a significant reduction in the incidence of diabetes. Animals injected with plasmid DNA encoding *Renilla reniformis* luciferase demonstrated a significant delay in the onset of diabetes. However, animals injected with plasmid DNA encoding intracellular GAD did not demonstrate either a significant reduction in the incidence of diabetes or a significant delay in the onset of diabetes, even though previous studies showed that injecting plasmid DNA encoding human GAD65 or a secreted GAD prevented islets inflammation (insulitis) in the pancreas of NOD mice. The present invention will now be disclosed in detail.

First, plasmids designated pND2-SRUC3, pND2-GAD65 and pND2-SGAD55 were constructed as disclosed in Liu, J. et al. (1999). Intramuscular injection of plasmid DNA encoding intracellular or secreted glutamic acid decarboxylase causes decreased insulitis in the non-obese diabetic mouse. *Gene Ther. Mol. Biol.* 3, 197–206. The cDNAs carried by the plasmids were respectively; sruc3, SEQ ID NO:1, encoding a secreted form of the soft coral *Renilla reniformis* luciferase; gad65, SEQ ID NO:2, encoding full-length human GAD65 protein; and sgad55, SEQ ID NO:3, a modified gad65 cDNA encoding a secreted truncated form of human GAD65, SEQ ID NO:2, that had an 88 amino acid amino-terminal region deletion removing a palmitoylation sequence and a Golgi targeting signal that prevents secretion of full-length GAD65 protein, leaving residues 265–1758 of SEQ ID NO:2. The deleted sequence was replaced with a human IL-2 sequence encoding a signal peptide, which was cleaved intracellularly before secretion. This truncated GAD65 protein (GAD55) contained all known epitopes recognized by antibodies from patients suffering from type 1 diabetes. Each cDNA was placed under transcriptional control of the cytomegalovirus promoter in plasmid pND2. In addition, each plasmid carried a CoL-E1 origin of replication and a gene encoding ampicillin resistance for amplification of plasmid DNA in the bacterium *Escherichia coli*.

The plasmid DNA was amplified in *E. coli* strain DH5-a, and isolated using the alkaline-lysis method followed by standard double-round cesium chloride purification. DNA quality and quantity were determined with a U.V. spectrophotometer ($A_{260}/A_{280}$ ratio greater than 1.8), and agarose gel electrophoresis. The plasmid DNA was then dissolved under sterile conditions in phosphate buffer saline (PBS) at a final concentration of 2 µg/µl, and stored at −20° C.

The plasmid DNA was administered intramuscularly to female NOD/MrkTac mice (Taconic Laboratories, Germantown, N.Y. US). Each animal was injected into each quadriceps muscle with 200 micrograms/leg at the age of four weeks using disposable tuberculin syringes fitted with 27G needle, and an identical set of injections two days later, for a total of 800 micrograms plasmid DNA/mouse. Three groups of mice received injections of pND-2 plasmid carrying either sruc3, SEQ ID NO:1, gad65, SEQ ID NO:2, or sgad55, SEQ ID NO:3, cDNA. An additional group of mice was left untreated as control. All mice received intraperitoneal injections of cyclophosphamide (200 mg/kg) at the age of 10 and 12 weeks to accelerate the onset of diabetes. The mice were kept in an animal facility under non-pathogen free conditions, and received injection of DNA under general anaesthesia using 66 mg/kg body weight ketamine (Phoenix Scientific, St Joseph, Mo. US), 7.5 mg/kg body weight oxylazine (Lloyd Laboratories, Shenandoa, Iowa US), and 1.5 mg/kg body weight acepromazine maleate (Fermenta Animal Health Co., Mo. US).

The onset of diabetes in the animals was determined by monitoring for glycosuria twice a week with Clinistix Reagent Strips for urine analysis (Bayer Corporation, Elkhart, Ind. US). Once glycosuria was present, a diagnosis of diabetes was confirmed when blood glucose levels were greater than 300 mg/deciliter on two consecutive days (using Accu-Chek™ Advantage (Roche Diagnostics Corporation, Indianapolis, Ind. US). Animals were sacrificed when diagnosed as diabetic, or at the end of the observation period when the animals were 18 weeks old. Statistical analysis of the results were performed using a Kaplan-Meier analysis with a log-rank and Mann-Whitney test to detect differences in prevention and delay of diabetes onset.

Referring now to FIG. 1, there is shown a graph depicting the results of administering the DNA given as the percent on non-diabetic, cyclophosphamide treated NOD mice given versus time, where the NOD mice were injected with plasmid DNA encoding full- length human GAD65 (filled boxes); SGAD55, a secreted form of human GAD65 (open boxes); SRUC3, a secreted form of the *Renilla reniformis* luciferase (open circles); or no injections of plasmid DNA (filled circles). As can be seen, the percentage of 18-week old animals that remained non-diabetic after receiving injection of plasmid pND2-SRUC3, pND2-GAD65 or pND2-SGAD55 was 18, 30 and 63, respectively, and 23 percent of untreated animals were free of diabetes at the end of the observation period. A Kaplan Meier plot of diabetes onset, together with statistical analysis, indicated that the mice which received injections of pND2-SGAD55 had a statistically significant reduction in diabetes when compared with untreated control (P=0.05, log-rank test). By contrast, mice that received injection of pND2-GAD65 did not show a statistically significant reduction in diabetes when compared with the same controls (P=0.37, log rank test). Although groups of untreated mice and mice that received injection of PND2-SRUC3 had a similar percentage of non-diabetic animals at the end of the observation period, injection of pND2-SRUC3 resulted in a significant delay in the onset of diabetes when compared to untreated controls using the Mann-Whitney test (P=0.01). Differences between the three groups of treated mice with respect to onset were not found to be statistically significant (P>0.13, log rank test).

Anti-luciferase and anti-GAD IgG and IgG1 antibody levels in mice sera were determined using ELISA to detect an immune response to luciferase and GAD polypeptides after injection of pND2-SRUC3, pND2-GAD65, and pND2-SGAD55 plasmids as follows. Blood was collected (0.5–1.5 ml) after heart puncture, and sera were obtained from samples after two centrifugations at 3,000×g for 10 minutes at 4° C., and 10 ml of 1% sodium azide was added to each sample. Ninety-six well microtiter plates (Dynex Technologies Inc., Chantilly, Va. US) were coated overnight at 4° C. with 100 ml phosphate buffer saline (PBS) containing 5 mM DTT, 100 mM beta-mercaptoethanol, and 10 mg/ml recombinant human GAD55 protein isolated from *E. coli*, or BSA. After blocking with 0.5% BSA in PBS for 2 hours at 37° C., serially diluted sera were added to wells and allowed to incubate for 2 hours at 37° C. Unbound proteins and antibodies were removed with four washes of PBS+0.1% Triton ×100 for 5 minutes at room temperature after each reaction. Alkaline phosphatase-conjugated Fab-specific anti-mouse IgG monoclonal antibodies (Sigma, St Louis, Mo. US) were diluted 1:40,000 in blocking buffer, added to wells, and incubated for 2 hours at 37° C. The relative amounts of bound antibodies were determined after addition of 100 ml alkaline phosphatase substrate Lumi-Phos Plus (Lumigen Inc., Southfield, Minn. US) to each well. Light emission catalyzed by alkaline phosphatase was measured in a ML3000 Luminometer (Dynex Technologies Inc., Chantilly, Va. US) after allowing the reaction to develop for 30 minutes at 37° C.

No increase in anti-luciferase IgG was detected in sera of mice that received injections of pND2-SRUC3 plasmid DNA, when compared with the other three groups of NOD mice and with a control group of untreated CD1 mice. Further, there were no apparent differences in the range of titers of anti-GAD IgG antibodies in sera of mice that received injections of pND2-GAD65 and pND2-SGAD55 plasmids, when compared with untreated controls and with mice that had received injection of plasmid pND2-SRUC3. However, titers of anti-GAD IgG were in generally higher in NOD mice than in CD1 controls, in contrast with titers of anti-luciferase IgG.

Because Th2 cells mediate a process that leads to production of IgG1 antibodies, IgG1 levels were determined and were used as a marker of whether a Th2 type of response was induced. IgG1 antibodies were determined using a corresponding protocol to that above, except that alkaline phosphatase-conjugated IgG1-specific anti-mouse IgG monoclonal antibodies (Zymed Laboratories Inc., South San Francisco, Calif. US) were used for detection at a dilution of 1:2,000.

No increase in anti-luciferase IgG1 titer was detected in sera of mice that received injections of plasmid pND2-SRUC3, when compared to other groups of NOD mice and with CD1 controls. Similarly, there was no increase in anti-GAD IgG1 titer in sera of NOD mice from the group that received injection of plasmid pND2-SRUC3 and the untreated group when compared to CD1 mice. By contrast, however, an increase in anti-GAD IgG1 titer was detected in several non-diabetic mice that received injections of plasmid pND2-SGAD55. In addition, some of the mice that received injection of plasmid pND2-GAD65 also showed increased anti-GAD IgG1 titer, but the increase did not always correlate with an absence of diabetes. None of the animals had titer of anti-luciferase and anti-GAD IgG2a antibodies above background.

These results indicate that insulitis scores obtained previously, Liu, J. et al., after injection of plasmid DNA encoding SRUC3, which did not decrease insulitis, and GAD65, which did decrease insulitis, were not predictive of diabetes prevention. Further, cellular location of human GAD polypeptide encoded by a genetic vaccine affects prevention of CYP-accelerated diabetes in the NOD mouse because injection of plasmid DNA encoding full-length intracellular GAD did not significantly prevent diabetes, while injection of plasmid encoding secreted GAD did decrease diabetes frequency. The decrease was accompanied by an increase in anti-GAD IgG1 titers, implicating the involvement of Th2 lymphocytes. In addition, the finding that both the injection of DNA encoding secreted foreign protein and secreted autoantigen delays the onset of diabetes implies that secretion of exogenous protein alone effects disease onset.

In one embodiment, the present invention is a method of preventing, delaying the onset of or treating diabetes in a patient. The method comprises, first, selecting a patient who is susceptible to developing diabetes, who is developing diabetes or who is diabetic. The selection can be made using standard methods as will be understood by those with skill in the art with reference to this disclosure. For example, the selection can be made by identifying in the patient the presence of anti-insulin or anti-GAD autoantibodies or both anti-insulin and or anti-GAD autoantibodies, the presence of increasing hyperglycemia, the patient the presence of glycosuria, the presence of a genetic predisposition to diabetes or more than one of these.

Next, the patient is administered one or more than one dose of a pharmaceutical agent comprising a polynucleotide encoding a secreted exogenous protein. In a preferred embodiment, the pharmaceutical agent is administered in a plurality of doses. In another preferred embodiment, the dose is between about 0.001 mg/Kg and about 10 mg/Kg. In another preferred embodiment, the dose is between about 0.01 mg/Kg and about 1 mg/Kg. In another preferred embodiment, the dose is about 0.1 mg/Kg. In another preferred embodiment, the dose is administered weekly between about 2 and about 10 times. In a particularly preferred embodiment, the dose is administered weekly 4 times.

In a particularly preferred embodiment, the secreted exogenous protein is a secreted *Renilla* luciferase comprising a sequence according to SEQ ID NO:1. In another particularly preferred embodiment, is a secreted form of human glutamic acid decarboxylase comprising a sequence according to SEQ ID NO:3. Additionally, the method can comprise, after administering, monitoring the patient for the development diabetes.

EXAMPLE 1

According to the present invention, the onset of diabetes in a patient is delayed or prevented, for example, as follows. First, the patient is selected based on the presence of circulating anti-insulin and anti-GAD autoantibodies. Next, the patient is injected intramuscularly with 0.1 mg/Kg of a pharmaceutical agent comprising a plasmid encoding a secreted form of human glutamic acid decarboxylase. The injection is repeated weekly for 3 weeks while the level of circulating anti-insulin and anti-GAD autoantibodies is monitored. The treatment is ended when the level of circulating anti-insulin and anti-GAD autoantibodies has returned to normal.

All references cited in this disclosure are incorporated herein by reference in their entirety. Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A method for delaying the onset of diabetes in a patient comprising:
   a) selecting a patient who is developing diabetes due to an autoimmune response to glutamic acid decarboxylase; and
   b) administering to the patient intramuscularly one or more than one dose of a pharmaceutical agent comprising a plasmid vector encoding a secreted form of human glutamic acid decarboxylase comprising SEQ ID NO: 3 under the control of a CMV promoter, causing the patient to express and secrete human glutamic acid decarboxylase and, thereby, causing a decrease in the autoimmune response to glutamic acid decarboxylase,
   wherein selecting the patient comprises identifying in the patient the presence of increasing hyperglycemia, glycosuria, or both increasing hyperglycemia and glycosuria, and then identifying in the patient the presence of anti-glutamic acid decarboxylase autoantibodies.

2. The method of claim 1, where selecting the patient comprises identifying in the patient the presence of a genetic predisposition to diabetes.

3. The method of claim 1, where the one or more than one dose is a plurality of doses.

* * * * *

SEQUENCE LISTING

<160> NUMBER OF SEQ ID NOS: 3

<210> SEQ ID NO 1
<211> LENGTH: 1271
<212> TYPE: DNA
<213> ORGANISM: Renilla reniformis

<400> SEQUENCE: 1

```
atgtacagga tgcaactcct gtcttgcatt gcactaagtc ttgcacttgt cacaaacagt      60
gcacctactg aattcagctt aaagatgact tcgaaagttt atgatccaga acaaaggaaa     120
cggatgataa ctggtccgca gtggtgggcc agatgtaaac aaatgaatgt tcttgattca     180
tttattaatt attatgattc agaaaaacat gcagaaaatg ctgttatttt tttacatggt     240
```

-continued

```
aacgcggcct cttcttattt atggcgacat gttgtgccac atattgagcc agtagcgcgg      300
tgtattatac cagatcttat tggtatgggc aaatcaggca aatctggtaa tggttcttat      360
aggttacttg atcattacaa atatcttact gcatggtttg aacttcttaa tttaccaaag      420
aagatcattt ttgtcggcca tgattggggt gcttgtttgg catttcatta tagctatgag      480
catcaagata agatcaaagc aatagttcac gctgaaagtg tagtagatgt gattgaatca      540
tgggatgaat ggcctgatat tgaagaagat attgcgttga tcaaatctga agaaggagaa      600
aaaatggttt tggagaataa cttcttcgtg gaaaccatgt tgccatcaaa aatcatgaga      660
aagttagaac cagaagaatt tgcagcatat cttgaaccat tcaaagagaa aggtgaagtt      720
cgtcgtccaa cattatcatg gcctcgtgaa atcccgttag taaaaggtgg taaacctgac      780
gttgtacaaa ttgttaggaa ttataatgct tatctacgtg caagtgatga tttaccaaaa      840
atgtttattg aatcggatcc aggattcttt tccaatgcta ttgttgaagg cgccaagaag      900
tttcctaata ctgaatttgt caaagtaaaa ggtcttcatt tttcgcaaga agatgcacct      960
gatgaaatgg gaaatatat caaatcgttc gttgagcgag ttctcaaaaa tgaacaataa     1020
ttactttggt tttttattta catttttccc gggtttaata atataaatgt cattttcaac     1080
aattttattt taactgaata tttcacaggg aacattcata tatgttgatt aatttagctc     1140
gaactttact ctgtcatatc attttggaat attacctctt tcaatgaaac tttataaaca     1200
gtggttcaat taattaatat atattataat tacatttgtt atgtaataaa ctcggtttta     1260
ttataaaaaa a                                                           1271
```

<210> SEQ ID NO 2
<211> LENGTH: 1758
<212> TYPE: DNA
<213> ORGANISM: Homo sapiens

<400> SEQUENCE: 2

```
atggcatctc cgggctctgg cttttggtct ttcgggtcgg aagatggctc tgggattcc       60
gagaatcccg gcacagcgcg agcctggtgc caagtggctc agaagttcac gggcggcatc      120
ggaaacaaac tgtgcgccct gctctacgga gacgccgaga gccggcgga gagcggcggg      180
agccaacccc gcggggccgc cgcccggaag gccgcctgcg cctgcgacca gaagccctgc      240
agctgctcca agtggatgt caactacgcg tttctccatg caacagacct gctgccggcg      300
tgtgatggag aaaggcccac tttggcgttt ctgcaagatg ttatgaacat tttacttcag      360
tatgtggtga aagtttcga tagatcaacc aaagtgattg atttccatta tcctaatgag      420
cttctccaag aatataattg ggaattggca gaccaaccac aaaatttgga ggaattttg      480
atgcattgcc aaacaactct aaaatatgca attaaaacag ggcatcctag atacttcaat     540
caactttcta ctggtttgga tatggttgga ttagcagcag actggctgac atcaacagca      600
aatactaaca tgttcaccta tgaaattgct ccagtatttg tgcttttgga atatgtcaca      660
ctaaagaaaa tgagagaaat cattggctgg ccagggggct ctggcgatgg gatattttct      720
cccggtggcg ccatatctaa catgtatgcc atgatgatcg cacgctttaa gatgttccca      780
gaagtcaagg agaaaggaat ggctgctctt cccaggctca ttgccttcac gtctgaacat     840
agtcattttt ctctcaagaa gggagctgca gcctaggga ttggaacaga cagcgtgatt      900
ctgattaaat gtgatgagag agggaaaatg attccatctg atcttgaaag aaggattctt      960
gaagccaaac agaaagggtt tgttcctttc ctcgtgagtg ccacagctgg aaccaccgtg     1020
```

-continued

```
tacggagcat ttgaccccct cttagctgtc gctgacattt gcaaaaagta taagatctgg    1080
atgcatgtgg atgcagcttg gggtggggga ttactgatgt cccgaaaaca caagtggaaa    1140
ctgagtggcg tggagagggc caactctgtg acgtggaatc cacacaagat gatgggagtc    1200
cctttgcagt gctctgctct cctggttaga gaagagggat tgatgcagaa ttgcaaccaa    1260
atgcatgcct cctacctctt tcagcaagat aaacattatg acctgtccta tgacactgga    1320
gacaaggcct tacagtgcgg acgccacgtt gatgttttta actatggct gatgtggagg     1380 gcaaagggga ctaccgggtt tgaagcgcat gttgataaat gttttggagtt ggcagagtat   1440 ttatacaaca tcataaaaaa ccgagaagga tatgagatgg tgtttgatgg gaagcctcag    1500
cacacaaatg tctgcttctg gtacattcct ccaagcttgc gtactctgga agacaatgaa    1560
gagagaatga gtcgcctctc gaaggtggct ccagtgatta agccagaat gatggagtat     1620 ggaaccacaa tggtcagcta ccaacccttg ggagacaagg tcaatttctt ccgcatggtc    1680
atctcaaacc cagcggcaac tcaccaagac attgacttcc tgattgaaga atagaacgc     1740 cttggacaag atttataa                                                  1758
```

```
<210> SEQ ID NO 3
<211> LENGTH: 1494
<212> TYPE: DNA
<213> ORGANISM: Homo sapiens

<400> SEQUENCE: 3
```

```
tacgcgtttc tccatgcaac agacctgctg ccggcgtgtg atggagaaag gcccactttg      60
gcgtttctgc aagatgttat gaacatttta cttcagtatg tggtgaaaag tttcgataga    120
tcaaccaaag tgattgattt ccattatcct aatgagcttc tccaagaata taattgggaa    180
ttggcagacc aaccacaaaa tttggaggaa atttttgatgc attgccaaac aactctaaaa   240
tatgcaatta aaacagggca tcctagatac ttcaatcaac tttctactgg tttggatatg    300
gttggattag cagcagactg gctgacatca acagcaaata ctaacatgtt cacctatgaa    360
attgctccag tatttgtgct tttggaatat gtcacactaa agaaaatgag agaaatcatt    420
ggctggccag ggggctctgg cgatgggata ttttctcccg gtggcgccat atctaacatg    480
tatgccatga tgatcgcacg ctttaagatg ttcccagaag tcaaggagaa aggaatggct    540
gctcttccca ggctcattgc cttcacgtct gaacatagtc atttttctct caagaaggga   600
gctgcagcct tagggattgg aacagacagc gtgattctga ttaaatgtga tgagagaggg    660
aaaatgattc catctgatct tgaaagaagg attcttgaag ccaaacagaa agggtttgtt    720
cctttcctcg tgagtgccac agctggaacc accgtgtacg gagcatttga ccccctctta    780
gctgtcgctg acatttgcaa aaagtataag atctggatgc atgtggatgc agcttggggt    840
gggggattac tgatgtcccg aaaacacaag tggaaactga gtggcgtgga gagggccaac    900
tctgtgacgt ggaatccaca caagatgatg ggagtcccct tgcagtgctc tgctctcctg    960
gttagagaag agggattgat gcagaattgc aaccaaatgc atgcctccta cctctttcag   1020
caagataaac attatgacct gtcctatgac actggagaca aggccttaca gtgcggacgc   1080
cacgttgatg tttttaaact atggctgatg tggagggcaa aggggactac cgggtttgaa   1140
gcgcatgttg ataaatgttt ggagttggca gagtatttat acaacatcat aaaaaaccga   1200
gaaggatatg agatggtgtt tgatgggaag cctcagcaca caaatgtctg cttctggtac   1260
attcctccaa gcttgcgtac tctggaagac aatgaagaga gaatgagtcg cctctcgaag   1320
gtggctccag tgattaaagc cagaatgatg gagtatggaa ccacaatggt cagctaccaa   1380
```

```
cccttgggag acaaggtcaa tttcttccgc atggtcatct caaacccagc ggcaactcac    1440
caagacattg acttcctgat tgaagaaata gaacgccttg gacaagattt ataa         1494
```